(12) United States Patent
Levine

(10) Patent No.: US 7,400,923 B1
(45) Date of Patent: Jul. 15, 2008

(54) MULTI-CHAMBER VENTRICULAR AUTOMATIC CAPTURE METHOD AND APPARATUS FOR MINIMIZING TRUE AND BLANKING PERIOD INDUCED VENTRICULAR UNDERSENSING

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 752 days.

(21) Appl. No.: 10/900,834

(22) Filed: Jul. 27, 2004

Related U.S. Application Data

(62) Division of application No. 09/973,300, filed on Oct. 9, 2001, now Pat. No. 6,819,955.

(51) Int. Cl.
*A61N 1/37* (2006.01)
(52) U.S. Cl. .......................................................... 607/28
(58) Field of Classification Search ............. 607/27–28, 607/9; 600/510
See application file for complete search history.

(56) References Cited

U.S. PATENT DOCUMENTS

| | | | |
|---|---|---|---|
| 4,401,119 A | 8/1983 | Herpers | 128/419 |
| 4,407,287 A | 10/1983 | Herpers | 28/419 |
| 4,712,556 A | 12/1987 | Baker, Jr. | 128/419 |
| 4,825,870 A | 5/1989 | Mann et al. | 128/419 |
| 4,967,746 A | 11/1990 | Vandegriff | 128/419 |
| 4,974,589 A | 12/1990 | Sholder | 128/419 |
| 5,591,214 A | 1/1997 | Lu | 607/9 |
| 5,776,167 A | 7/1998 | Levine et al. | 607/9 |
| 5,861,012 A | 1/1999 | Stroebel | |
| 6,128,532 A | 10/2000 | Stoop et al. | 607/9 |

FOREIGN PATENT DOCUMENTS

| | | |
|---|---|---|
| EP | 1123716 B1 | 8/2001 |
| WO | WO 99/30777 | 6/1999 |

OTHER PUBLICATIONS

See References Listed on attached PTO-1449 filed in parent case, U.S. Appl. No. 09/973,300. Copies are not attached.
Levine, Paul A., M.D., Analysis of AV Universal (DDD) Pacemaker Rhythms, Clin. Prog. Pacing and Electrophysiol., vol. 2, No. 1, pp. 54-70 (1984).
Levine, Paul A., M.D., Normal and Abnormal Rhythms Associated with Dual-Chamber Pacemakers, Cardiology Clinics, vol. 3, No. 4, pp. 595-616 (Nov. 1985).
NonFinal Office Action, mailed Mar. 15, 2004: Parent U.S. Appl. No. 09/973,300.
Notice of Allowance, mailed Jul. 14, 2004: Parent U.S. Appl. No. 09/973,300.

*Primary Examiner*—Mark W Bockelman

(57) ABSTRACT

An implantable cardiac stimulation device and associated method perform a true or blanking period ventricular undersensing detection algorithm in response to ventricular loss of capture not associated with fusion or a change in capture threshold. The test identifies an originating cause of loss of capture, which may be ventricular undersensing of intrinsic R-waves or premature ventricular contractions occurring during a ventricular blanking period or atrial undersensing of P-waves resulting in blanking period ventricular undersensing. A corrective action is taken to reduce the likelihood of blanking period ventricular undersensing by automatically adjusting device operating parameters. The corrective action may include automatic adjustment of atrial sensitivity, shortening of the ventricular blanking period, or adjustment of the base stimulation rate. Minimizing the blanking period ventricular undersensing improves device performance by avoiding back-up stimulation and minimizing the risk of pacemaker competition-induced arrhythmias.

13 Claims, 8 Drawing Sheets

MULTI-CHAMBER VENTRICULAR AUTOMATIC CAPTURE METHOD AND APPARATUS FOR MINIMIZING TRUE AND BLANKING PERIOD INDUCED VENTRICULAR UNDERSENSING

CROSS-REFERENCE TO RELATED APPLICATIONS

This application is a divisional of copending U.S. patent application Ser. No. 09/973,300, filed Oct. 9, 2001.

FIELD OF THE INVENTION

This invention relates generally to programmable cardiac stimulating devices. Particularly, the present invention is directed to an implantable stimulation device and associated method capable of automatically adjusting sensitivity and blanking interval settings in a way that minimizes the frequency of ventricular stimulation competition with natural ventricular depolarizations. More specifically, the present cardiac stimulation device offers various automatic capture features, and further allows automatic atrial sensitivity adjustment, automatic ventricular sensitivity adjustment, automatic mode switching, automatic base rate adjustment, and automatic AV interval adjustment.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium).

Stimulation may be delivered to the atrial and/or the ventricular heart chambers depending on the location and severity of the conduction disorder. In dual chamber, demand-type pacemakers, commonly referred to as DDD pacemakers, an atrial channel and a ventricular channel each include a sense amplifier to detect cardiac activity in the respective chamber and an output circuit for delivering stimulation pulses to the respective chamber. If the atrial channel does not detect an intrinsic atrial depolarization signal (a P-wave), a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrial-ventricular interval (AV interval or delay), a stimulation pulse is delivered to the ventricle to cause ventricular contraction. In this way, atrial-ventricular synchrony is maintained by coordinating the delivery of ventricular output in response to a sensed or paced atrial event.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

The capture "threshold" is defined as the lowest stimulation pulse energy at which consistent capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used and the electrode positioning. In addition, there are physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. Typically, the internal myocardial electrogram (EGM) signals received on cardiac sensing electrodes are sampled and processed in a way that allows detection of an "evoked response" following delivery of a stimulation pulse. If a loss of capture is detected, that is no evoked response is detected, by such "capture-verification" algorithms, a high-energy safety pulse that will ensure capture can be immediately delivered to prevent a missed heart beat. After which, the cardiac pacing device automatically performs a threshold test in order to re-determine the capture threshold and automatically adjust the stimulation pulse energy to be just above threshold. This approach, called "automatic capture", improves the cardiac stimulation device performance in at least two ways: 1) by verifying that the stimulation pulse delivered to the patient's heart has been effective; and 2) greatly increasing the device's battery longevity by conserving the energy used to generate stimulation pulses.

In dual chamber stimulation devices, therefore, accurate sensing of both evoked responses and the intrinsic deflection of the naturally occurring cardiac events, also referred to as "intrinsic" events, is crucial for achieving atrial-ventricular synchrony. However, sometimes stimulation pulses generated by, for example, the atrial channel of the pacemaker may be detected by the sensing circuitry of the ventricular channel and mistakenly identified as a naturally occurring ventricular event. This phenomenon is commonly referred to as "crosstalk." An atrial stimulation pulse mistakenly detected by the ventricular channel will cause ventricular stimulation output to be inhibited when in fact stimulation is needed, resulting in a "missed beat" or asystole, an undesirable situation.

A common approach for preventing crosstalk is to apply a "blanking interval" to the sensing circuitry of the channel in which crosstalk is anticipated. For example, during application of an atrial stimulation pulse, and for a short time thereafter, the ventricular sensing circuitry is disengaged to prevent the detection of the atrial stimulation pulse and the associated afterpotential signal.

The blanking interval is preferably kept as short as possible to prevent undersensing of natural cardiac events, but it must be long enough to prevent crosstalk. Undersensing of a naturally occurring cardiac event may cause the pacemaker to apply an inappropriate stimulus to the heart. For example, if the pacemaker fails to detect a late-cycle ventricular depolarization because the intrinsic deflection of the EGM occurred during the ventricular blanking interval, an unnecessary stimulation pulse will be delivered to the ventricle. This stimulation pulse may fail to capture the heart because it is delivered during the physiologic refractory period following the native depolarization.

The loss of capture will invoke the automatic capture feature causing a high-energy, back-up pulse to be delivered. This back-up pulse could be delivered coincidentally with the repolarization phase of the myocardium, represented by the T-wave portion of the ECG signal. Delivery of a high-energy stimulation pulse that is certain to capture the heart during the T-wave can induce a potentially life-threatening ventricular tachycardia in a patient susceptible to cardiac arrhythmias. Thus, the automatic capture feature, which is intended as a safety feature, may have an adverse effect even during normal operation of the stimulation device. It is therefore extremely important to minimize ventricular stimulation competition with intrinsic ventricular activity due to blanking period ventricular undersensing as just described.

One approach to avoiding T-wave stimulation that might occur as a result of ventricular fusion or pseudofusion which can be interpreted by the automatic capture algorithm as noncapture resulting in delivery of the high-output back-up pulse is to extend the AV interval on the next cycle. If the presumed loss of capture was actually due to fusion with intact AV nodal conduction, the native ventricular complex will be sensed and inhibit the subsequent ventricular output. However, this approach does not remedy the problem of blanking period ventricular undersensing of ventricular depolarizations.

A method for minimizing the blanking period to avoid blanking period undersensing while still preventing crosstalk involves a total blanking period that includes an absolute blanking period and a relative blanking period. The absolute blanking interval may be kept very short to prevent sensing of afterpotential signals associated with the atrial stimulation pulse. The absolute blanking period is followed by a relative blanking period, during which any sensed events are presumed to be residual effects of crosstalk. If no event is detected during the relative refractory period, the blanking period is terminated. An event detection during the relative blanking period will therefore restart a second blanking period until the crosstalk signal has ended. This approach is effective in minimizing the ventricular blanking period in the absence of crosstalk while still preventing crosstalk from occurring when a residual signal can be detected on the ventricular channel.

The situation of a true intrinsic deflection associated with a native cardiac depolarization occurring during the absolute blanking period, and going undetected, has not been fully addressed heretofore. What is needed is a method to determine if a loss of capture event is actually the result of blanking period ventricular undersensing. Blanking period ventricular undersensing may have caused delivery of a ventricular output at a time when capture is not possible, resulting in a loss of capture and the subsequent delivery of a back-up pulse that may be effective since it is delivered later in the cycle. If blanking period ventricular undersensing is suspected, a method for adjusting the stimulation device operating parameters to minimize the occurrences of blanking period ventricular undersensing is desirable. In this way, the potential for triggering a life-threatening tachycardia by unnecessarily stimulating on a T-wave is reduced.

SUMMARY OF THE INVENTION

The present invention addresses the foregoing concerns by providing an implantable cardiac stimulation device capable of automatically adjusting sensitivity and blanking interval settings in a way that minimizes the frequency of ventricular stimulation competition with natural ventricular depolarizations. The cardiac stimulation device offers various automatic capture features such as: automatically detecting capture or loss of capture on the primary pulse, preventing loss of heart rate support by delivery of a significantly higher output back-up pulse, automatically determining capture threshold, and automatically adjusting stimulation pulse energy. It further allows automatic atrial sensitivity adjustment, automatic ventricular sensitivity adjustment, automatic mode switching, automatic base rate adjustment, and automatic AV interval adjustment.

One feature of the present invention is to provide a method for determining when a ventricular loss of capture is likely to have been caused by blanking period ventricular undersensing, and, in this situation, to inhibit the delivery of unnecessary high energy stimulation pulses associated with the automatic capture algorithm. This important feature is realized by an automatic "blanking period undersensing detection" algorithm. By implementing this new feature, device performance is improved by avoiding back-up stimulation invoked by automatic capture in a setting of ventricular undersensing, thus minimizing the risk of competition-induced, life-threatening arrhythmias.

Device performance is further improved by increasing the automatic operation of the device in interpreting its own function and appropriately adjusting the operating parameters. Increasing automatic operations can reduce the need for unscheduled office visits to a medical practitioner and reduces the need for high interpretive skills of an attending medical provider in interpreting the cardiac stimulation system function.

Another feature of the present invention is to provide a method for adjusting the stimulation device operating parameters such that blanking period ventricular undersensing is minimized.

Yet another feature of the present invention is to discriminate between ventricular loss of capture events as a consequence of functional loss of capture associated with true atrial undersensing, true ventricular undersensing, blanking period ventricular undersensing, and actual loss of capture due to subthreshold stimulation.

Still another feature of the present invention is to automatically adjust device operating parameters to alleviate an identified cause of loss of capture.

The foregoing and other features of the present invention are realized by providing an implantable cardiac stimulation device equipped with cardiac data acquisition capabilities. A preferred embodiment of the stimulation device includes a control system for controlling the operation of the device and executing various test algorithms including automatic capture verification and a ventricular blanking period detection algorithm; a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses. In addition, the device includes memory for storing operational parameters for the control system. The device also includes a telemetry circuit for communicating with an external programmer.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As described above, the present invention aims at providing a method for determining when ventricular blanking period undersensing is suspected to be causing ventricular loss of capture. This method also takes corrective action to reduce the likelihood of ventricular blanking period undersensing. The methods of the present invention are intended for use in a dual-chamber or multi-chamber cardiac stimulation system possessing various features of automatic capture. While the present invention could be successfully implemented in numerous cardiac stimulation devices, for the sake of convenience, one cardiac stimulation system in which the methods of the present invention could be implemented, will be described in conjunction with FIGS. 1 and 2. The methods of the present invention will then be described in detail in conjunction with FIGS. 3 through 6B.

Figure 1:
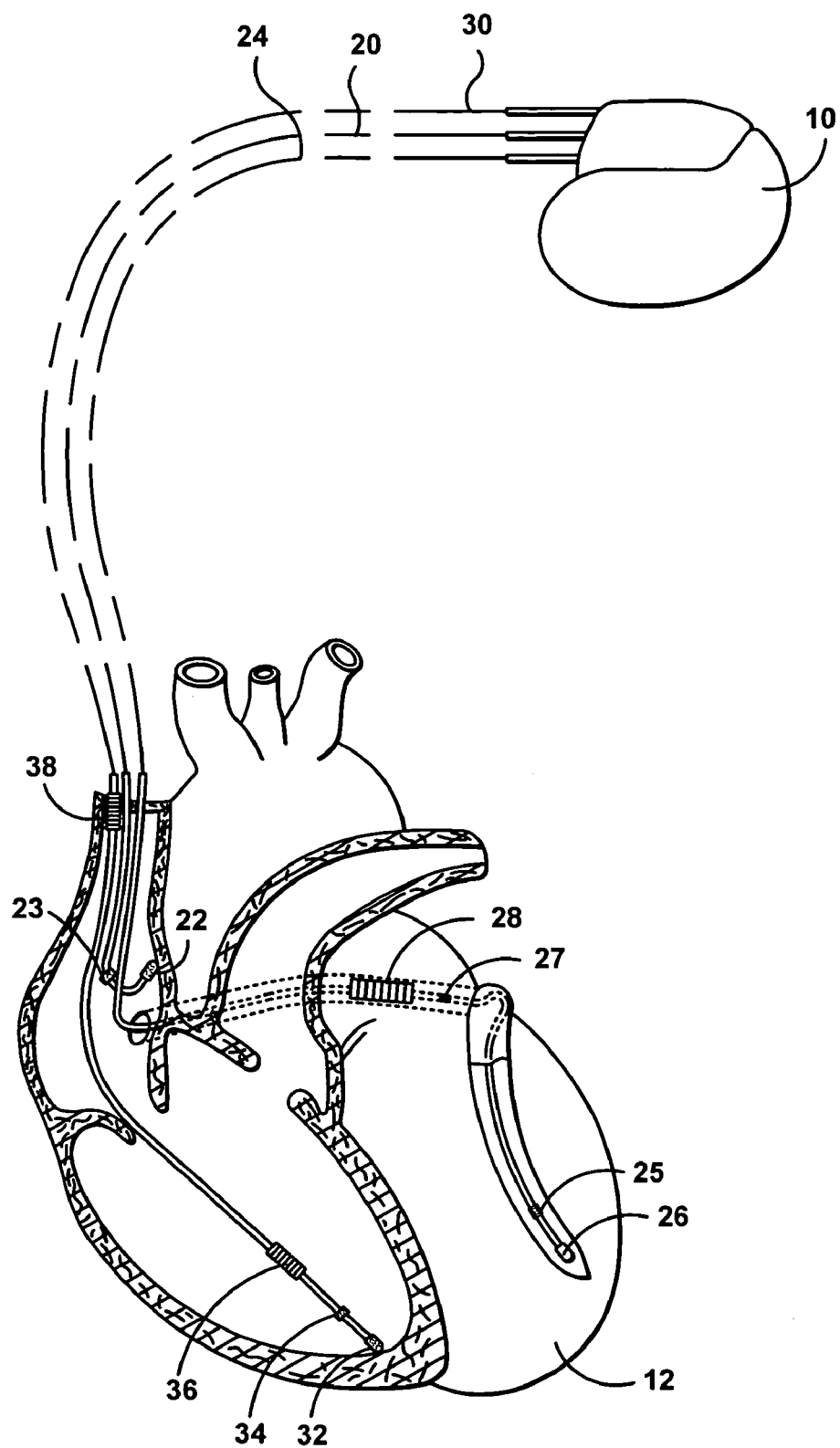
FIG. 1 is a simplified diagram illustrating an implantable stimulation device in electrical communication with at least three leads implanted into a patient's heart for delivering multi-chamber stimulation and shock therapy.

As shown in FIG. 1, a stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. As used herein, the coronary sinus region also refers to any location within or adjacent to the left ventricle, which may be accessed by either an endocardial lead or an epicardial lead.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
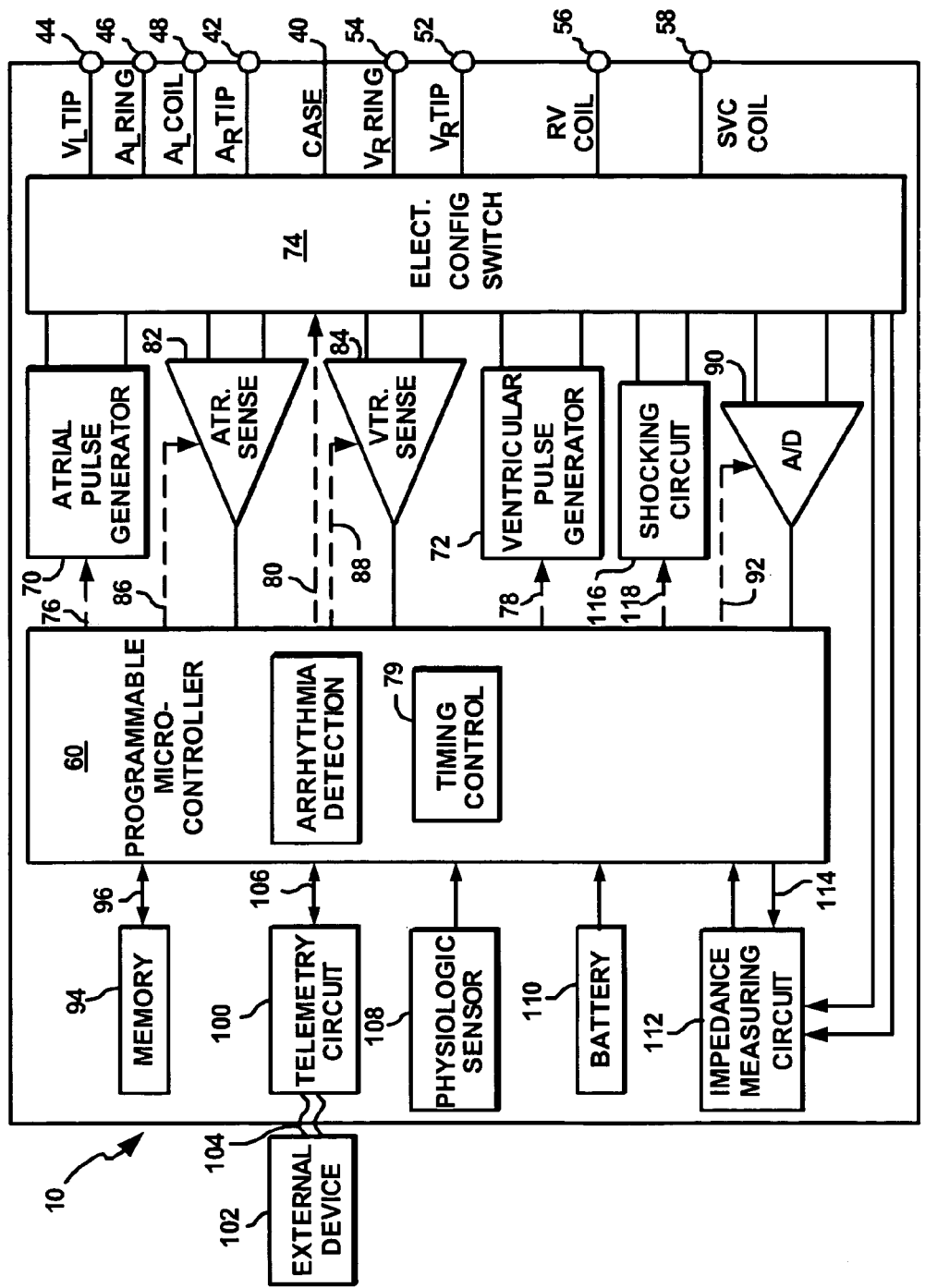
FIG. 2 is a functional block diagram of a multi-chamber implantable stimulation device illustrating the basic elements of a stimulation device that can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The stimulation device 10 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. The microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred.

The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the signal amplitude or another feature of the signal characteristic of an evoked response, determines if capture has occurred.

Capture detection may occur on a beat-by-beat basis or on a sampled basis. In addition, a capture threshold search is automatically performed on a periodic basis such as every 8 hours. A capture threshold test may also be performed whenever the capture verification routine fails to verify capture following a stimulation pulse. A capture threshold search would begin at a desired starting point (either a high energy level or the level at which capture is currently occurring) and decrease the energy level until capture is lost. The system then begins to increment the output in smaller steps than those which were used to decrease the output. The lowest value at which capture is established is known as the capture threshold. Thereafter, the stimulating energy is set equal to the threshold plus a defined voltage. This is known as the working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In one preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse.

As further shown in FIG. 2, the device 10 includes an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118.

The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted earlier, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
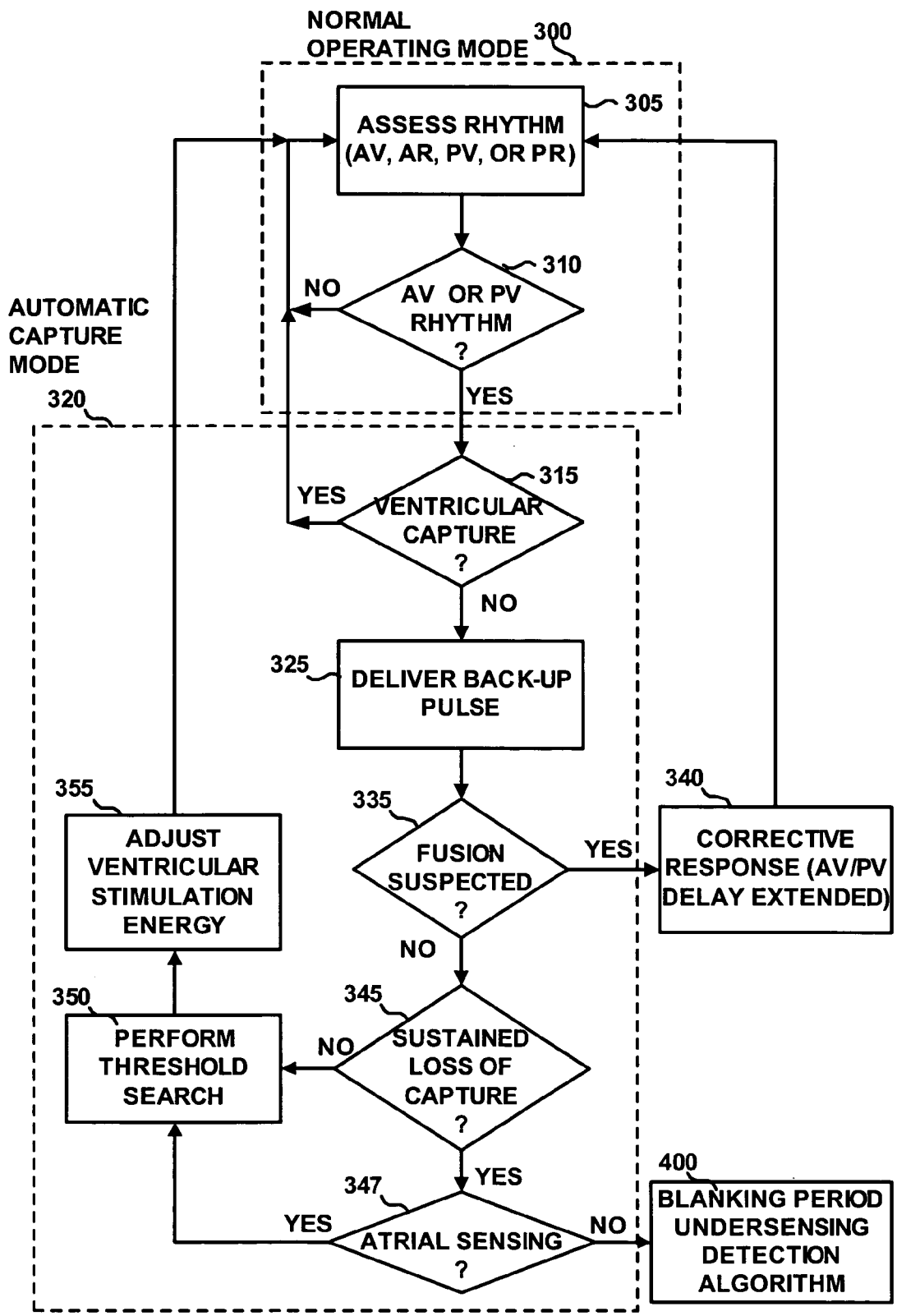
FIG. 3 is a flow chart describing an overview of the operation of one embodiment of the present invention for triggering a blanking period undersensing detection algorithm.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

In FIG. 3, three operating modes of operation of the stimulation device 10 are shown: a normal operating mode 300, an automatic capture mode 320, and a blanking period undersensing detection mode 400. The normal operating mode 300 represents the normal sensing and stimulation operations of device 10 according to the programmed operating parameters. The automatic capture mode 320 includes the capture verification, threshold testing, and automatic adjustment of the stimulation energy routines which are normally included in an automatic capture feature.

Figure 4:
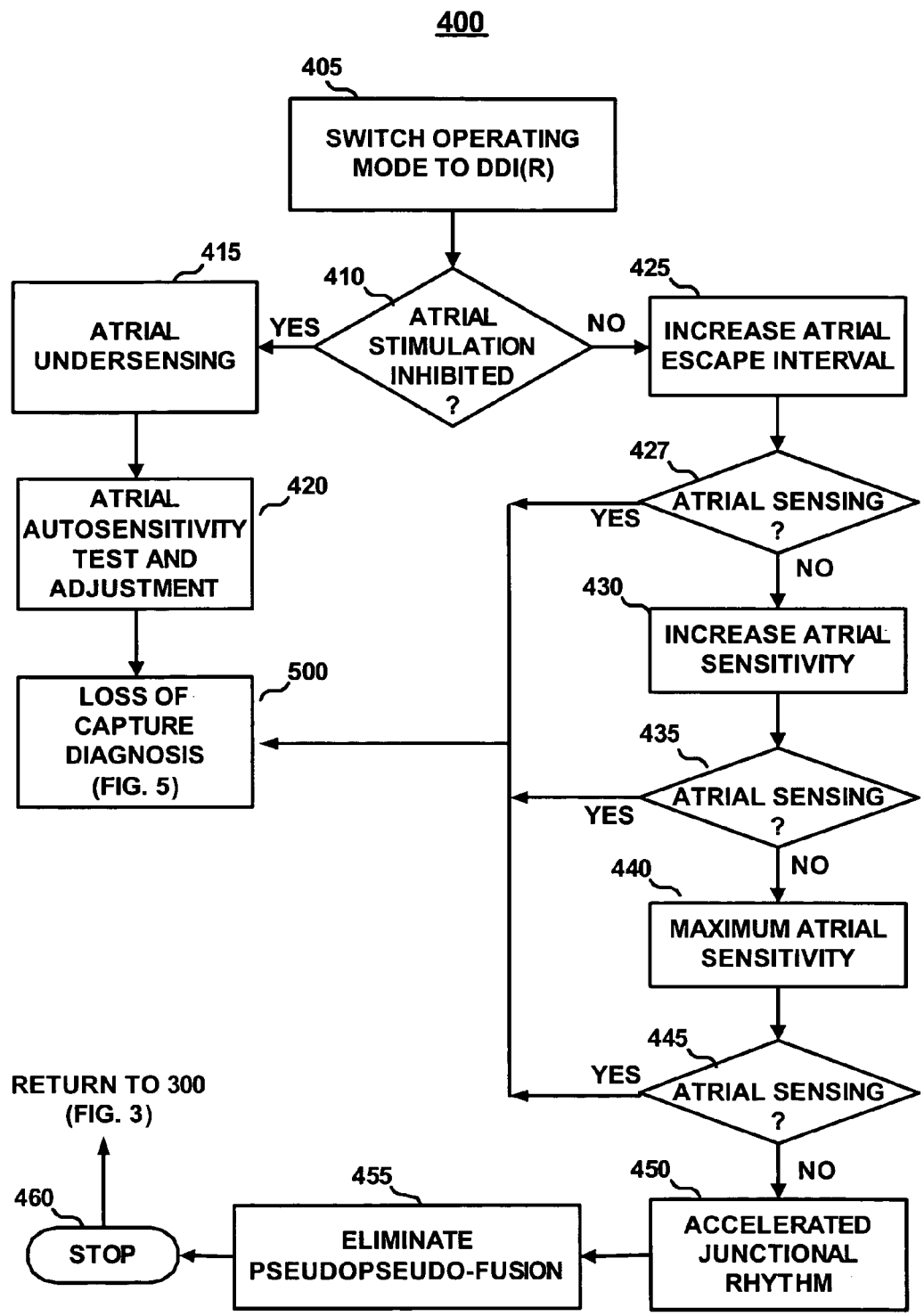
FIG. 4 is a flow chart illustrating a blanking period undersensing detection process, included in one embodiment of the present invention, to be performed in patients with intact atrial-ventricular conduction.

The blanking period undersensing detection mode 400 represents a novel feature provided by the present invention which will be described in greater detail in conjunction with FIGS. 4 and 5. The relationships between these three operating modes, as illustrated in FIG. 3, will now be explained.

During the normal operating mode 300, the microcontroller 60 of device 10 continually assesses the cardiac rhythm at step 305. The rhythm may be classified according to whether the atrium is being sensed or stimulated and whether the ventricle is being sensed or stimulated. A 'P' denotes atrial sensing of the P-wave whereas an 'A' denotes atrial stimulation. Likewise, an 'R' denotes ventricular sensing and a 'V' denotes ventricular stimulation. Thus the predominate cardiac rhythm may be described as a 'PR rhythm', an 'AR rhythm', a 'PV rhythm' or an 'AV rhythm'.

If, at decision step 310, the rhythm is determined to be one of ventricular stimulation, that is an AV or PV rhythm, the automatic capture mode 320 is invoked at decision step 315 to determine if ventricular capture occurred following the ventricular stimulation pulse. As long as ventricular capture is maintained, the device 10 returns to the normal operating mode 300.

However, if ventricular capture is not verified at decision step 315, the automatic capture mode 320 continues. At step 325, a high-energy back stimulation pulse is delivered in order to maintain the desired heart rate. Upon a first loss of capture detection, fusion is suspected at decision step 335. Fusion is defined as the delivery of a stimulation pulse concurrently with a native cardiac depolarization. The resulting intracardiac signal is typically distorted and may not be detected as capture.

If the EGM deflection is not detected, the automatic capture mode 320 determines that loss of capture has occurred and delivers a back-up stimulation pulse. It should be clear that other fusion detection methods may alternatively be used.

In case this first loss of capture detection is a coincidental fusion event, a corrective action is taken at step 340 in order to reduce the likelihood of fusion reoccurring. An exemplary corrective action includes, for example, extending the delay between an atrial sensed event (P), or an atrial stimulated event (A), and the delivery of ventricular stimulation (V). Thus, at step 340, the AV delay and PV delay settings are extended to allow more time for the native depolarization to take place before delivering ventricular stimulation. Device 10 then returns to the normal operating mode 300 (step 305).

If, however, ventricular loss of capture is found to reoccur but has not yet occurred for a predefined number of consecutive stimulation cycles, e.g. three to five cycles, as determined at decision step 345, the automatic capture mode 320 proceeds with performing a threshold search at step 350. The ventricular stimulation energy is automatically adjusted at step 355.

If loss of capture still continues for a predefined number of consecutive cycles, as determined at decision step 345, and stable atrial sensing is not occurring as determined at decision step 347, the repeated loss of capture may be associated with blanking period ventricular undersensing. The blanking period ventricular undersensing detection algorithm is therefore called upon at step 400.

If, however, stable atrial sensing is occurring, as determined at decision step 347, the automatic capture mode 320 may proceed by performing another threshold test and automatically adjusting ventricular stimulation pulse energy as necessary, at steps 350 and 355. During atrial sensing, no ventricular blanking period is generated so there is no need to proceed with the blanking period ventricular undersensing detection mode 400.

To summarize the operations depicted in FIG. 3, on an initial ventricular loss of capture detection, an adjustment is made to avoid fusion in case the detected loss of capture was in fact a missed detection due to fusion. If a subsequent ventricular loss of capture detection is made, a threshold search is performed in case the detected loss of capture was a true loss of capture due to an actual rise in threshold. If ventricular loss of capture persists for another predefined number of consecutive cycles and the predominant rhythm is atrial stimulation, the blanking period undersensing detection mode 400 is called upon to determine if the sustained loss of capture is due to blanking period ventricular undersensing.

The details of the blanking period undersensing detection mode (or process) 400 will now be described in conjunction with FIG. 4. First, the blanking period undersensing detection mode 400 ensures that appropriate atrial sensing is established. During normal device 10 operation, if atrial sensing is absent, so that an atrial output pulse is delivered every cardiac cycle, a ventricular blanking period will be triggered every cardiac cycle.

This ventricular blanking may be causing the ventricular channel to be "blinded" to a native depolarization that occurs within the blanking period. This phenomenon has been described as "blanking period ventricular undersensing" and is also termed "functional undersensing". The undetected native depolarization may be a normal R-wave following an undetected P-wave due to atrial undersensing, or it may be a junctional beat (e.g. a ventricular depolarization arising from the AV node of the heart's conduction system), or a ventricular ectopic beat. The latter two beats would not be preceded by an atrial depolarization at all.

In all three of these cases, however, a ventricular stimulation pulse delivered by the device 10 following the ventricular blanking period would be delivered during physiologic refractory and cause a ventricular loss of capture detection. It will be seen that the present invention provides a method to determine which, if any, of these three conditions is present and likely to be causing the apparent ventricular loss of capture.

Therefore, the first step 405 of the blanking period undersensing detection process 400 is to verify appropriate atrial sensing. At step 405, the operating mode of device 10 is temporarily changed from the programmed setting (normally DDD, dual chamber stimulation and sensing in a demand mode) to a dual chamber non-tracking mode, i.e. DDI[R]. In this DDI mode, the device 10 will still sense and stimulate in both the atrial and ventricular chambers of the heart, but a sensed R-wave will inhibit atrial stimulation, even if the atrial channel does not sense a native P-wave.

The rationale for changing to a non-tracking mode at step 405 can be explained as follows. If stable R-wave sensing occurs during the non-tracking stimulation mode, then atrial output will be inhibited every time an R-wave is sensed. If no atrial sensing precedes the sensed R-waves, then atrial undersensing is likely. This atrial undersensing during the previous normal operating mode 300 would have resulted in atrial stimulation, triggering regular ventricular blanking periods, which may have led to blanking period ventricular undersensing and the subsequent loss of capture detection.

After the temporary mode switch at step 405, the mode 400 determines if atrial stimulation is now inhibited by stable R-wave sensing at decision step 410, it being presumed that atrial sensing is still absent as determined at step 347 of FIG. 3. If atrial sensing is inhibited by R-wave sensing and atrial sensing is still absent, then atrial undersensing is possible.

This presumed diagnosis of atrial undersensing is made at step 415. An automatic atrial sensitivity test is performed, and the atrial sensitivity setting is adjusted as necessary at step 420. The process 400 then calls upon the loss of capture diagnosis subroutine 500, as will be described later in conjunction with FIG. 5.

If, at decision step 410, the atrial stimulation output is not inhibited by R-wave sensing, then the atrial escape interval is increased at step 425 to allow more time to sense the native cardiac rhythm. If atrial sensing is established at the reduced rate, as determined at decision step 427, then process 400 calls upon the loss of capture diagnosis subroutine 500.

If, however, atrial sensing is still not established at decision step 427, the atrial sensitivity is increased at step 430 by a predefined amount. At step 435, process 400 determines if atrial sensing now occurs at the reduced rate (i.e., at an increased atrial escape interval) and increased atrial sensitivity. If so, the loss of capture diagnosis subroutine 500 is called upon.

If atrial sensing still does not occur as determined at decision step 435, the atrial sensitivity is set to a maximum sensitivity at step 440. If atrial sensing is now established, as determined at decision step 445, process 400 calls upon subroutine 500 to diagnose the loss of ventricular capture. If atrial sensing still does not occur at decision step 445, a junctional rhythm is diagnosed at step 450.

A junctional rhythm arises from the AV node rather than the SA node of the heart's conduction system. Regular QRS complexes may occur but are not preceded by intrinsic atrial activity. During normal operation of device 10, the atrial channel will not sense an atrial event because no atrial event will be present and therefore deliver an atrial stimulation pulse. The atrial stimulation pulse may coincide with the onset of the native QRS but has not caused the ventricular depolarization. This phenomenon is known as a pseudopseudofusion complex. The atrial stimulation pulse will also trigger a ventricular blanking period, which may coincide with the native QRS complex arising from the junctional rhythm.

Therefore, at step 455, the programmed DDD operation mode of the device 10 is restored but at an increased base rate in order to avoid pseudopseudofusion beats and to supercede the rate of the junctional rhythm. The blanking period undersensing detection process 400 is then terminated at step 460, and device 10 returns to the normal operating mode 300 but at the increased base rate.

Figure 5A:
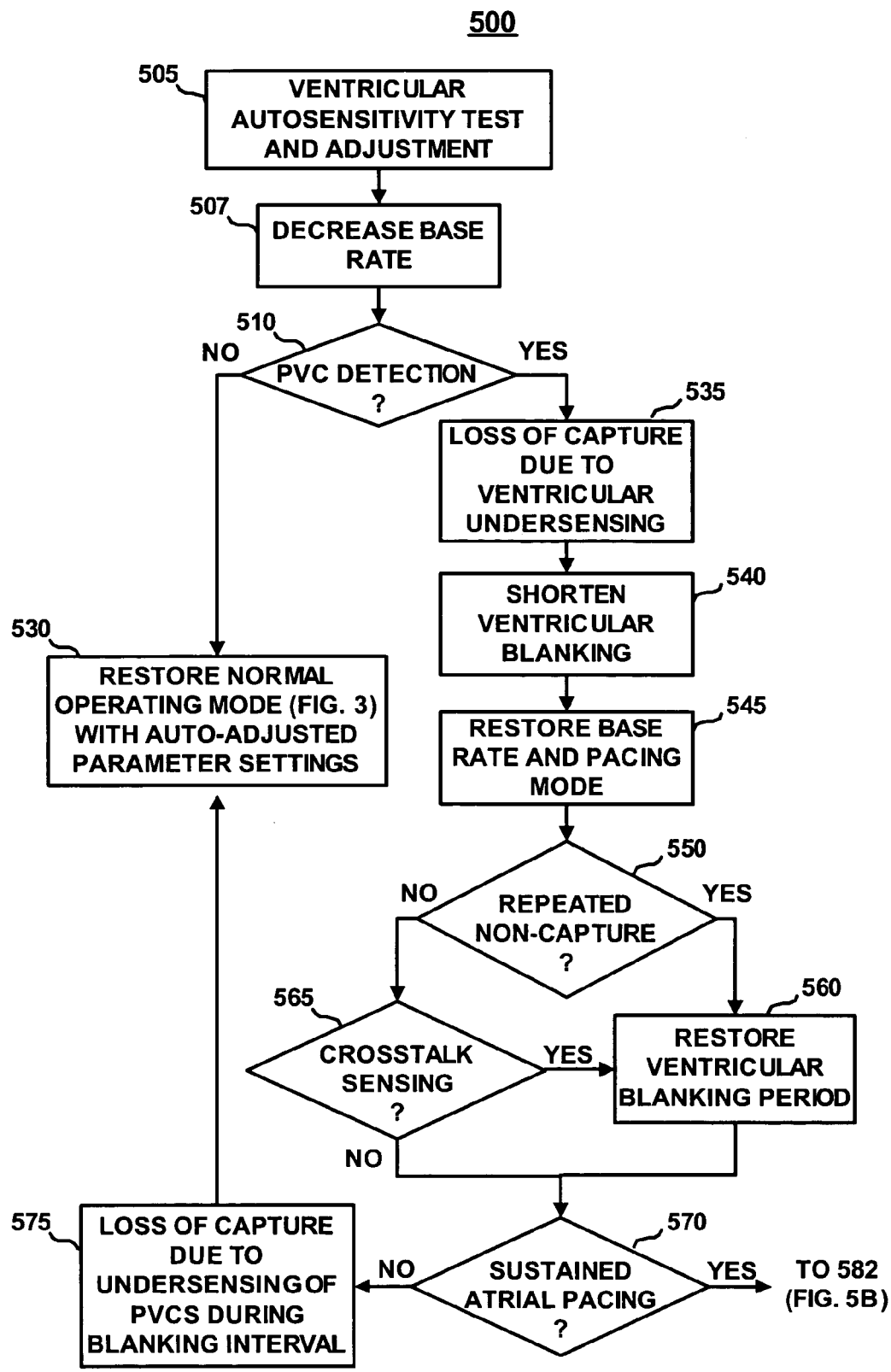
FIGS. 5A and 5B represent a flow chart illustrating a loss of capture diagnosis subroutine that is called upon by the blanking period undersensing detection process of FIG. 4.
Figure 5B:
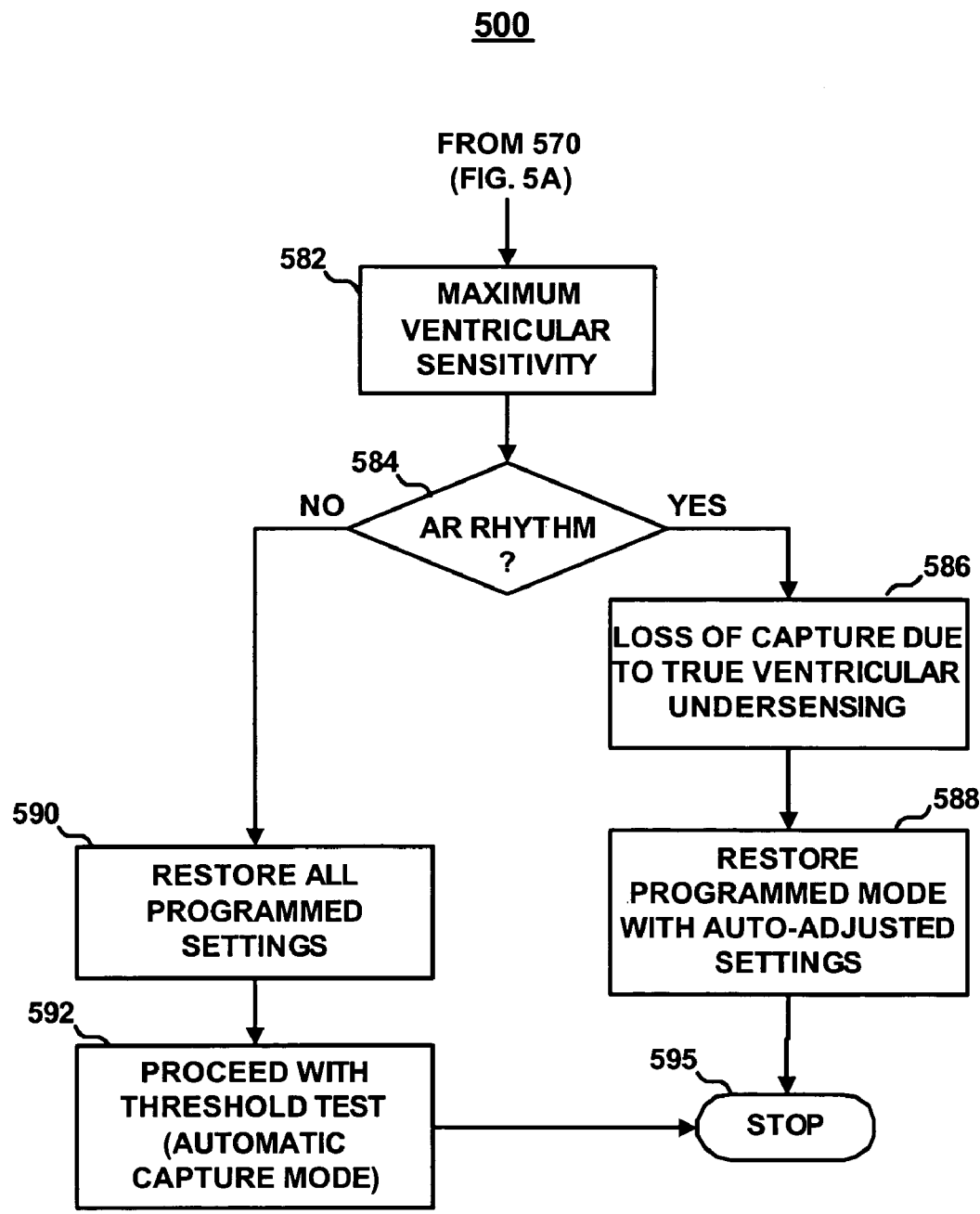

Referring to FIGS. 5A and 5B, the loss of capture diagnosis subroutine (or process) 500 will now be described. Beginning at step 505, the ventricular sensitivity is automatically tested and adjusted if necessary. This step 505 verifies that ventricular undersensing was not the root cause of the ventricular loss of capture. If the ventricular sensitivity is determined to be too low during the normal device 10 operation, ventricular stimulation pulses may have been delivered coincidentally with undetected native depolarizations, resulting in a loss of capture detection.

Once appropriate ventricular sensitivity has been reaffirmed, the base stimulation rate is reduced to a predefined rate below the normally programmed rate at step 507. The rhythm is then monitored at decision step 510 to determine if premature ventricular contractions (PVCs) are detected.

When regular atrial and ventricular sensing (PR sensing) occurs with each sensed P-wave followed by one sensed R-wave, then premature ventricular contractions (PVCs) do not exist. However, if detected R-waves exist that are not preceded by an atrial event, knowing that appropriate atrial sensing has been established, the detected R-wave can be classified as a premature ventricular contraction or as a AV junctional beat.

If premature ventricular contractions (PVCs) are not detected at decision step 510, then the subroutine 500 restores the programmed operating parameters (base rate and DDD mode) with the automatically adjusted sensitivity settings at step 530. The diagnosis of atrial undersensing made during process 400 (FIG. 4) remains as the most likely cause of the ventricular loss of capture. The adjusted atrial sensitivity setting may thus improve sensing of atrial events and prevent further loss of capture events due to blanking period ventricular undersensing.

If premature ventricular contractions (PVCs) are detected at decision step 510, a preliminary diagnosis of blanking period ventricular undersensing of the premature ventricular contractions is made at step 535. The ventricular blanking period may be too long to allow adequate sensing of native ventricular depolarizations, therefore, at step 540, the ventricular blanking period is shortened.

The programmed base stimulation rate and pacing mode (e.g. DDD) are restored at step 545. The subroutine 500 then determines at decision step 550 if ventricular loss of capture detections reoccur with the next ventricular stimulation events following an atrial output. If ventricular loss of capture reoccurs following atrial output, the action of shortening the ventricular blanking period was not effective in preventing failure of ventricular sensing with the subsequent loss of capture associated with the ventricular output pulse. Therefore, the ventricular blanking period is restored to the previous setting at step 560.

If ventricular loss of capture does not reoccur at decision step 550, then the subroutine 500 verifies that crosstalk has not been introduced by the shortened ventricular blanking period at decision step 565. If the ventricular blanking interval has been made too short, the ventricular channel may incorrectly detect the afterpolarization signal associated with the atrial stimulation pulse as a ventricular event.

If crosstalk is occurring, it can be identified by setting a crosstalk detection window immediately following the shortened ventricular blanking period. If repeated event sensing by the ventricular sensing circuit 84 occurs during the crosstalk detection window, then the ventricular blanking period is considered too short to reliably prevent crosstalk. Thus, if crosstalk is identified at decision step 565, the ventricular blanking period is restored to its previous setting at step 560. If crosstalk is detected, the ventricular output pulse is the high output pulse associated with the back-up pulse rather than the lower output associated with the automatic capture-algorithm. In the setting of crosstalk as recognized by the pacing system, the automatic capture algorithm is disabled for that one cycle.

Next, at decision step 570, the subroutine 500 determines if sustained atrial stimulation has returned at the restored base rate and stimulation mode. If atrial stimulation has returned, the loss of capture diagnosis of blanking period ventricular undersensing of premature ventricular contractions is confirmed at step 575. The normal operating parameters are restored at step 530 with the exception of any adjustments made to the atrial sensitivity, ventricular sensitivity and ventricular blanking period. The device 10 is thus returned to the normal operating mode 300 (FIG. 3).

Hence, a diagnosis of functional undersensing of premature ventricular contractions has been made. If the shortened ventricular blanking period did not result in crosstalk at decision step 565, then the likelihood of functional undersensing has been successfully reduced. Hence, the likelihood of delivering a high-energy back up stimulation pulse during the T-wave has been reduced, improving the safety of the cardiac stimulation device 10.

If the shortened ventricular blanking period did result in crosstalk at decision step 565, such that the previous blanking period setting had to be restored (step 560), then no corrective action has been taken to reduce the likelihood of functional undersensing. However, the incidence of crosstalk is less desirable than functional undersensing. Crosstalk may result in asystole ("missed heartbeat") because ventricular stimulation will be withheld. Therefore, the elimination of crosstalk takes precedence over reducing the likelihood of functional undersensing by shortening the ventricular blanking period.

Referring to FIG. 5B, if atrial stimulation does return after restoring the base rate and stimulation mode, as determined at decision step 570 of FIG. 5A, the ventricular sensitivity is set to a maximum at step 582. An intrinsic R-wave, particularly a ventricular ectopic beat since it arises from a different focus, may be too small to be sensed at the programmed ventricular sensitivity. The consequence to the patient would be the same as blanking period ventricular undersensing: delivery of a primary output pulse when the myocardium is physiologically refractory resulting in loss of capture and delivery of the back-up pulse, possibly during the intrinsic T-wave. If R-wave sensing is established at the maximum ventricular sensitivity setting at step 582, then the previous ventricular loss of capture events are presumed to be due to ventricular undersensing at step 586. At step 588, the programmed settings are restored with the exception of the adjusted settings for atrial sensitivity, ventricular sensitivity and ventricular blanking period. Device 10 is thus returned to the normal operation mode 300 (FIG. 3).

If R-wave sensing is not established at the maximum ventricular sensitivity, the diagnosis of the loss of capture events due to undersensing is inconclusive. Therefore, all programmed settings are restored at step 590. The device 10 is returned to the automatic capture mode 320 of FIG. 3 at step 592, to proceed with performing a threshold test, in order to determine if an actual rise in ventricular threshold has caused the loss of capture. The loss of capture diagnosis subroutine 500 is then terminated at step 595.

Referring to FIG. 6, an alternative embodiment of the present invention is described for use in patients inflicted with high-degree or total AV block. In patients with AV block, a mode switch to DDI would be inappropriate since conduction of an atrial sensed or stimulated event will not occur. Therefore, an alternative blanking period undersensing detection process 600 is shown in FIG. 6 that would be executed in place of process 400 of FIG. 4 in patients with AV block.

In the embodiment of FIG. 6, the first step 605 of this alternative blanking period undersensing detection process 600 is to switch the operating mode to VDD. In a VDD mode, the atrial output is eliminated and thus the ventricular blanking period is also eliminated. By eliminating the ventricular blanking period, an assessment can be made as to whether a repetitious ventricular loss of capture may have been caused by functional undersensing. Thus, in a preferred embodiment of the present invention, the operating mode switch (to VDD or DDI for example) at the beginning of a blanking period undersensing detection algorithm is programmable to allow a sensing and stimulation mode to be selected that accommodates the most appropriate blanking period undersensing detection process (400 or 600) in a particular patient.

At step 610, the base rate is reduced to a predefined rate below the programmed rate. The device 10 will now be sensing in the atrium and either sensing or stimulating in the ventricle (VDD mode). In other terms, the rhythm will be either a PV rhythm or a PR rhythm. If a stable PR rhythm is predominate, as determined at decision step 612, blanking period ventricular undersensing is suspected. Stable R-wave sensing at a rate approximately equal to the previous atrial stimulation rate when ventricular loss of capture was detected would suggest that, during normal device operation, the ventricular blanking period induced by atrial stimulation caused functional undersensing, leading to repeated ventricular loss of capture. The programmed mode is restored at step 614 but at an adjusted base rate so that the native ventricular events do not coincide with the ventricular blanking period.

If, at decision step 612, ventricular stimulation is occurring such that the predominate rhythm identified is a PV rhythm, process 600 proceeds to decision step 625 to determine if ventricular capture is now occurring at the reduced base rate. If ventricular loss of capture persists, then the detected loss of capture may be the result of an actual rise in ventricular threshold. At step 620, the automatic capture mode 320 is called upon to proceed with a threshold test.

If, however, ventricular capture returns at decision step 615, a determination is made at decision step 625 as to whether the existing PV rhythm is approximately equal to the base rate. The ventricular output at the base rate in the VDD mode is equivalent to a VVI mode, where no atrial rhythm is sensed and the ventricle is stimulated at the base rate. If the ventricular stimulation at the base rate is occurring, then atrial undersensing is suspected as the root cause of the previous ventricular loss of capture detections. Atrial undersensing would induce sustained atrial stimulation during the normal DDD operating mode of device 10, thus inducing regular ventricular blanking periods possibly leading to functional undersensing and the delivery of a ventricular stimulation pulse during the physiologic refractory period.

Figure 6A:
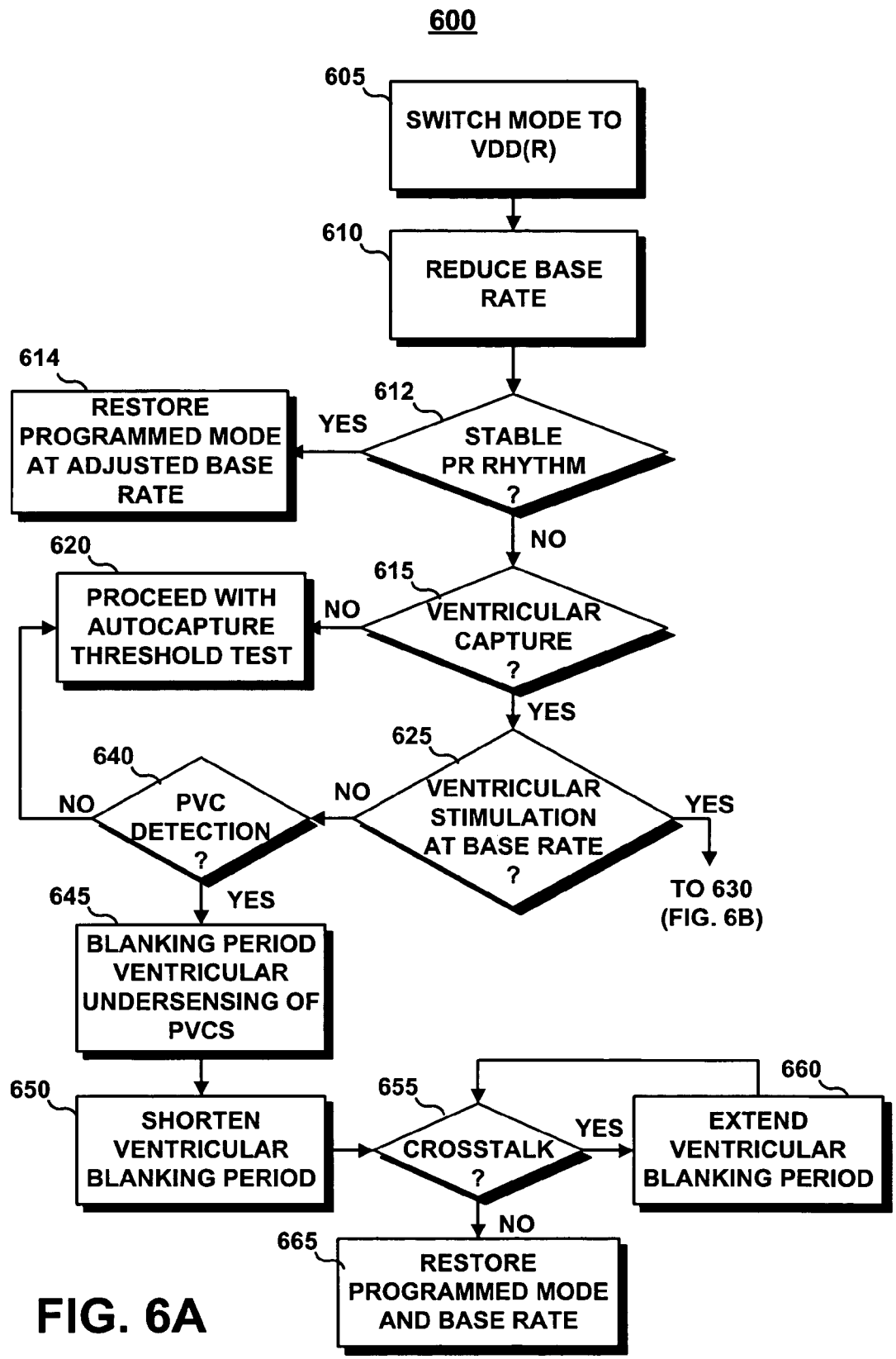
FIGS. 6A and 6B represent a flow chart illustrating a blanking period undersensing detection process, included in one embodiment of the present invention, to be performed in patients with high-degree or total atrial-ventricular conduction block.
Figure 6B:
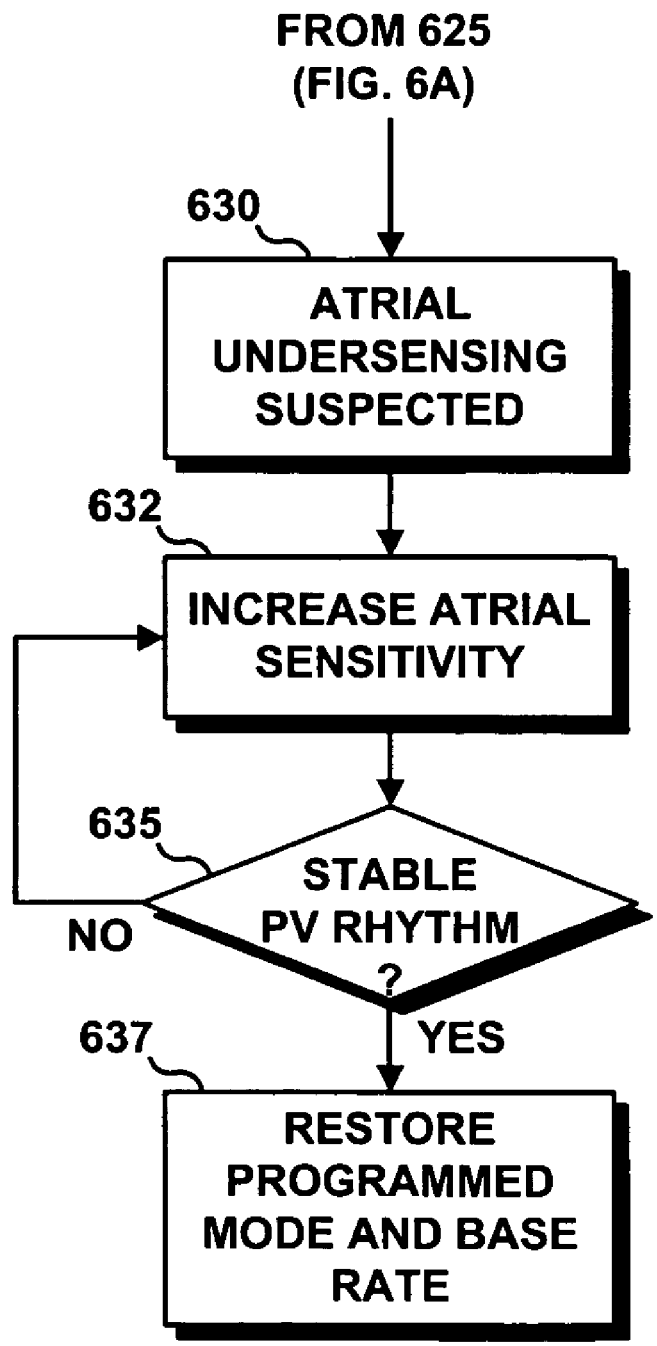

Referring to FIG. 6B, this diagnosis of atrial undersensing is made at step 630. Therefore, at step 632, the atrial sensitivity is increased to re-establish appropriate atrial sensing. At decision step 635, the rhythm is monitored to determine if a stable PV rhythm has been established by restoring atrial sensing. If not, the atrial sensitivity is increased again at step 632 until appropriate atrial sensing and a stable PV rhythm are established at decision step 635. Next, at step 637, the programmed mode and base rate are restored with the adjusted atrial sensitivity. The device 10 is thus returned to the normal operating mode 300.

Referring back to FIG. 6A, if ventricular stimulation does not occur at the base rate as determined at decision step 625, then a PV rhythm exists above the base rate. In this case, the process 600 proceeds to step 640 to determine if premature ventricular contractions (PVCs) are detected. Premature ventricular contractions are indicated if R-waves are detected without a preceding P-wave. If no premature ventricular contractions are detected, the automatic capture mode or process 320 is called upon at step 620 to proceed with a threshold test. Blanking period ventricular undersensing is not suspected.

If, on the other hand, premature ventricular contractions are detected at decision step 640, particularly if they are occurring near the programmed base rate during which ventricular loss of capture first occurred, then blanking period ventricular undersensing of premature ventricular contractions is diagnosed at step 645 as the cause of the initial ventricular loss of capture. As a result, the ventricular blanking period is shortened by a predefined interval, at step 650.

At decision step 655, the process 600 verifies that the shortened blanking period did not introduce crosstalk. If crosstalk was introduced, the ventricular blanking period is increased by a predefined interval at step 660 until crosstalk is eliminated as determined by returning to decision step 655. The programmed mode and base rate are then restored at step 665 with the adjusted ventricular blanking period. The shortened ventricular blanking period is expected to reduce the occurrence of functional undersensing and thereby reduce the likelihood of T-wave stimulation, improving the safety of device 10. If the ventricular blanking period had to be extended back to the original setting in order to eliminate crosstalk, then functional undersensing may reoccur, however crosstalk is a less desirable situation.

Thus, a method has been described that detects the possibility of functional undersensing in response to repeated ventricular loss of capture detections. This method further provides a method of assessing whether functional or actual loss of sensing is present along with remedial adjustments of programmed operating parameters that will lessen the likelihood of functional or true undersensing from reoccurring. The cardiac stimulation device is improved by the disclosed method because the chances of inadvertent T-wave stimulation due to blanking period or other ventricular undersensing has been reduced, improving the overall safety of the cardiac stimulation device performance.

While detailed descriptions of specific embodiments of the present invention have been provided, it would be apparent to those reasonably skilled in the art that numerous variations of the methods disclosed are possible which would not deviate from the scope of the present invention. The descriptions provided herein, therefore, are for the sake of illustration and are not intended to be exclusive.

What is claimed is:

1. A cardiac stimulation device capable of performing automatic capture verification, for detecting blanking period ventricular undersensing, comprising:
- a pulse generator that selectively generates stimulation pulses;
- a lead, connected to the pulse generator, that delivers the stimulation pulses to one or more cardiac chambers;
- a timing circuit that is responsive to a stimulation pulse to set a blanking period following the delivery of the stimulation pulse;
- a control circuit that determines if a ventricular loss of capture event is possibly due to blanking period ventricular undersensing; and
- wherein the control circuit is operative to adjust one or more operating parameters if blanking period ventricular undersensing is suspected to have caused the ventricular loss of capture.

2. The device of claim 1, wherein the control circuit further continuously assesses a cardiac rhythm to determine if ventricular stimulation occurs following atrial stimulation.

3. The device of claim 2, wherein whenever ventricular stimulation occurs following atrial stimulation, the control circuit performs ventricular capture verification.

4. The device of claim 3, wherein if ventricular loss of capture is detected, the control circuit delivers a high-energy back-up stimulation pulse.

5. The device of claim 4, wherein the control circuit further determines if a fusion event is suspected to have occurred.

6. The device of claim 5, wherein if a fusion event is suspected to have occurred, the control circuit initiates corrective action.

7. The device of claim 6, wherein the corrective action includes an extended AV delay setting.

8. The device of claim 6, wherein if a fusion event is not suspected, the control circuit invokes a blanking period ventricular undersensing detection test following a number of ventricular loss of capture events.

9. The device of claim 6, wherein if a fusion event is not suspected, the control circuit invokes a blanking period ventricular undersensing detection test upon every ventricular loss of capture event immediately following an atrial stimulation pulse.

10. The device of claim 1, wherein the control circuit determines that the ventricular loss of capture event is due to blanking period ventricular undersensing by detecting an occurrence of atrial undersensing.

11. The device of claim 10, wherein the control circuit detects an occurrence of atrial undersensing by switching a mode of operation to any one of: DDI or DDIR.

12. The device of claim 10, wherein the control circuit detects an occurrence of atrial undersensing by ventricular sensing of an R-wave without atrial sensing of a preceding P-wave.

13. The method of claim 10, wherein if atrial undersensing occurs, the control circuit considers a ventricular blanking period as an originating cause of ventricular loss of capture.

* * * * *